(12) United States Patent
Markworth et al.

(10) Patent No.: US 7,833,248 B2
(45) Date of Patent: Nov. 16, 2010

(54) SPINAL CROSS-CONNECTOR

(75) Inventors: Aaron D. Markworth, Saddle Brook, NJ (US); Mahmoud F. Abdelgany, Rockaway, NJ (US)

(73) Assignee: Custom Spine, Inc., Parsippany, NJ (US)

( * ) Notice: Subject to any disclaimer, the term of this patent is extended or adjusted under 35 U.S.C. 154(b) by 604 days.

(21) Appl. No.: 11/567,380

(22) Filed: Dec. 6, 2006

(65) Prior Publication Data
US 2007/0213723 A1 Sep. 13, 2007

Related U.S. Application Data

(63) Continuation-in-part of application No. 11/373,386, filed on Mar. 10, 2006.

(51) Int. Cl.
*A61B 17/70* (2006.01)
(52) U.S. Cl. .................. 606/253; 606/246; 606/279; 403/64
(58) Field of Classification Search ......... 606/246–253, 606/278–279; 403/64, 169, 170, 174, 178
See application file for complete search history.

(56) References Cited

U.S. PATENT DOCUMENTS

| 2,683,329 | A |   | 7/1954  | Kobler |
|-----------|---|---|---------|--------|
| 3,054,321 | A |   | 9/1962  | Macchia |
| 5,100,420 | A |   | 3/1992  | Green et al. |
| 5,312,405 | A |   | 5/1994  | Korotko et al. |
| 5,330,473 | A | * | 7/1994  | Howland ............ 606/250 |
| 5,334,203 | A |   | 8/1994  | Wagner |
| 5,498,263 | A |   | 3/1996  | DiNello et al. |
| 5,522,816 | A | * | 6/1996  | Dinello et al. ......... 606/252 |
| 5,688,272 | A |   | 11/1997 | Montague et al. |
| 5,727,899 | A |   | 3/1998  | Dobrovolny |
| 5,735,851 | A |   | 4/1998  | Errico et al. |
| 5,743,911 | A | * | 4/1998  | Cotrel ................. 606/250 |
| 5,989,250 | A |   | 11/1999 | Wagner et al. |
| 6,030,389 | A |   | 2/2000  | Wagner et al. |
| 6,187,005 | B1 |  | 2/2001  | Brace et al. |
| 6,217,578 | B1 |  | 4/2001  | Crozet et al. |
| 6,299,614 | B1 |  | 10/2001 | Kretschmer et al. |
| 6,302,882 | B1 |  | 10/2001 | Lin et al. |

(Continued)

FOREIGN PATENT DOCUMENTS

WO    WO0150968    7/2001

*Primary Examiner*—Eduardo C Robert
*Assistant Examiner*—Steven J Cotroneo
(74) *Attorney, Agent, or Firm*—Rahman LLC

(57) ABSTRACT

A cross-connector assembly construct and a method of locking comprises a flexible clip contacting a longitudinal member; a housing component contacting the flexible clip, wherein the housing component comprises a conical ramp towards a bottom end of the housing component; a locking mechanism contacting the housing component and adapted to engage the flexible clip; and a connecting member contacting the housing component. The flexible clip comprises a flexible bias member adapted to retain the longitudinal member. The flexible clip comprises a non-symmetrical socket portion; and a clip portion attached to the non-symmetrical socket portion, the clip portion being adapted to retain the longitudinal member. The locking mechanism comprises a camming pin adapted to be housed within the housing component and engage the flexible clip causing the longitudinal member to become affixed to the flexible clip; and a blocker mechanism operatively connected to the housing component and the connecting member.

20 Claims, 11 Drawing Sheets

U.S. PATENT DOCUMENTS

| | | |
|---|---|---|
| 6,432,108 B1 | 8/2002 | Burgess et al. |
| 6,524,310 B1 | 2/2003 | Lombardo et al. |
| 6,736,817 B2 | 5/2004 | Troxell et al. |
| 6,761,721 B2 | 7/2004 | Burgess et al. |
| 6,783,526 B1 | 8/2004 | Lin et al. |
| 6,793,657 B2 | 9/2004 | Lee et al. |
| 6,875,211 B2 | 4/2005 | Nichols et al. |
| 6,890,334 B2 | 5/2005 | Brace et al. |
| 7,524,326 B2 | 4/2009 | Dierks |
| 2003/0163133 A1 | 8/2003 | Altarac et al. |
| 2004/0049188 A1 | 3/2004 | Slivka et al. |
| 2005/0070918 A1 | 3/2005 | Zwirnmann et al. |
| 2005/0113831 A1 | 5/2005 | Franck et al. |
| 2005/0192572 A1 | 9/2005 | Abdelgany et al. |
| 2005/0192573 A1 | 9/2005 | Abdelgany et al. |
| 2005/0228377 A1 | 10/2005 | Chao et al. |
| 2005/0234450 A1 | 10/2005 | Barker |
| 2007/0049932 A1* | 3/2007 | Richelsoph et al. ........... 606/61 |

* cited by examiner

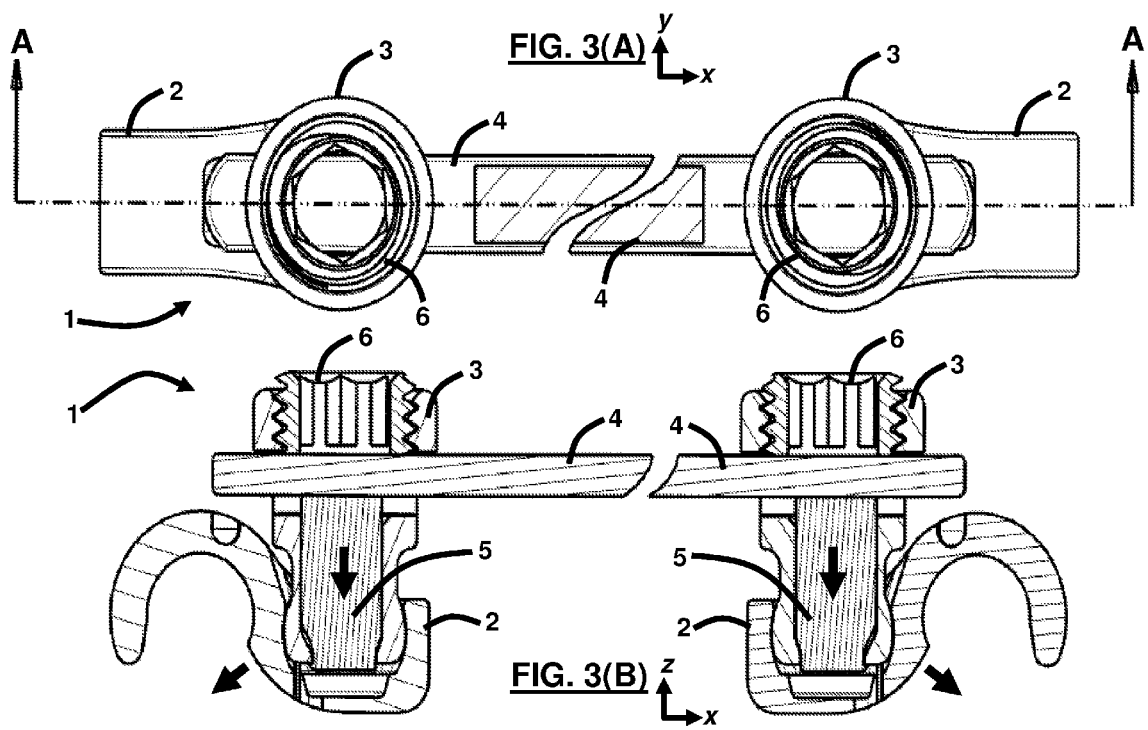

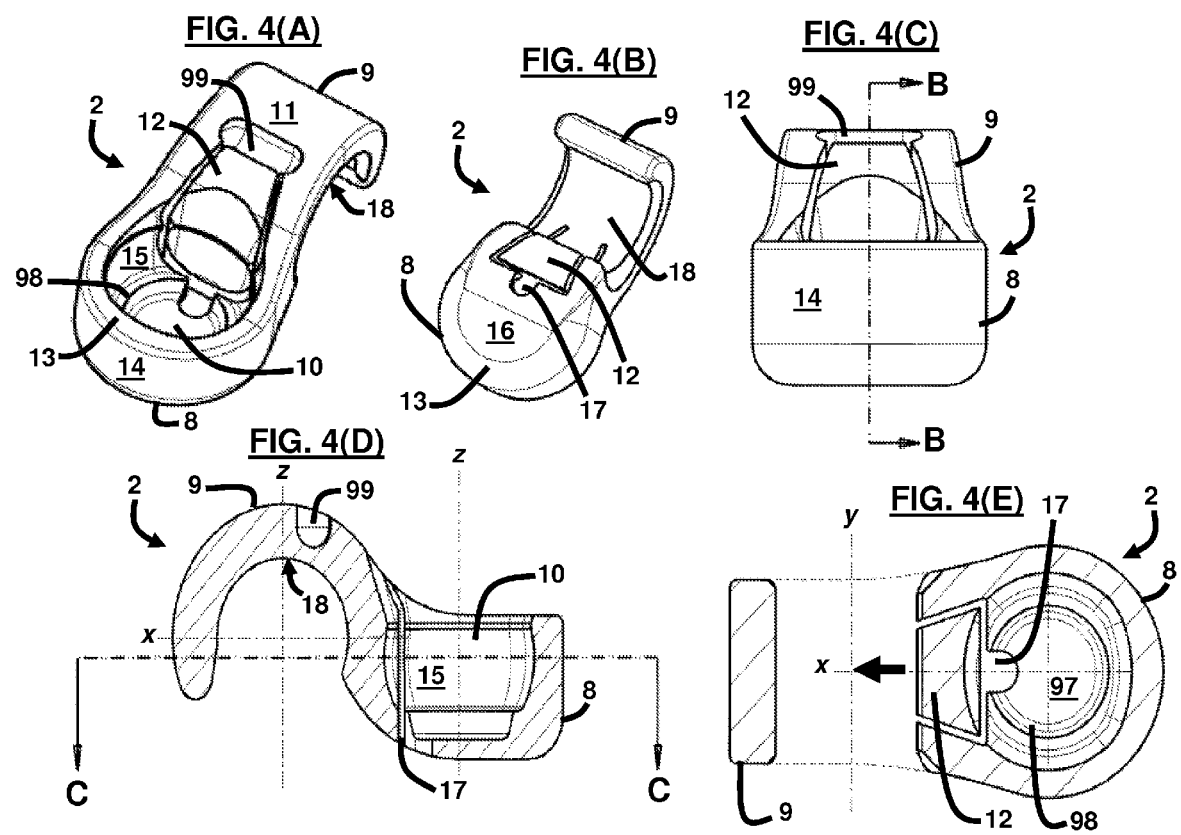

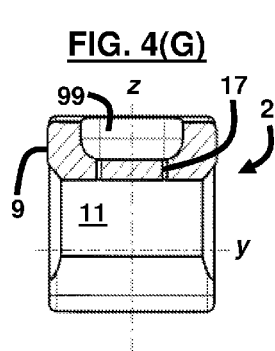
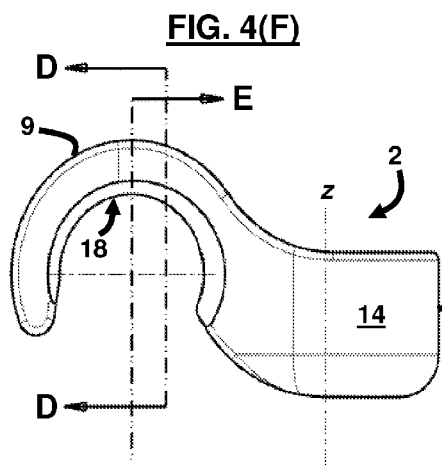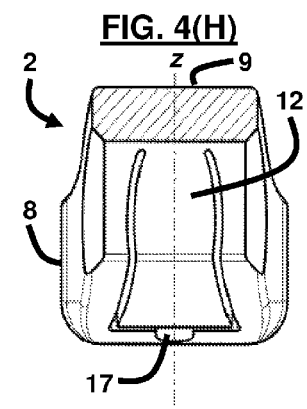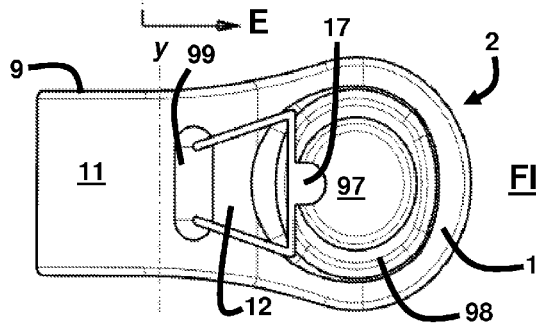

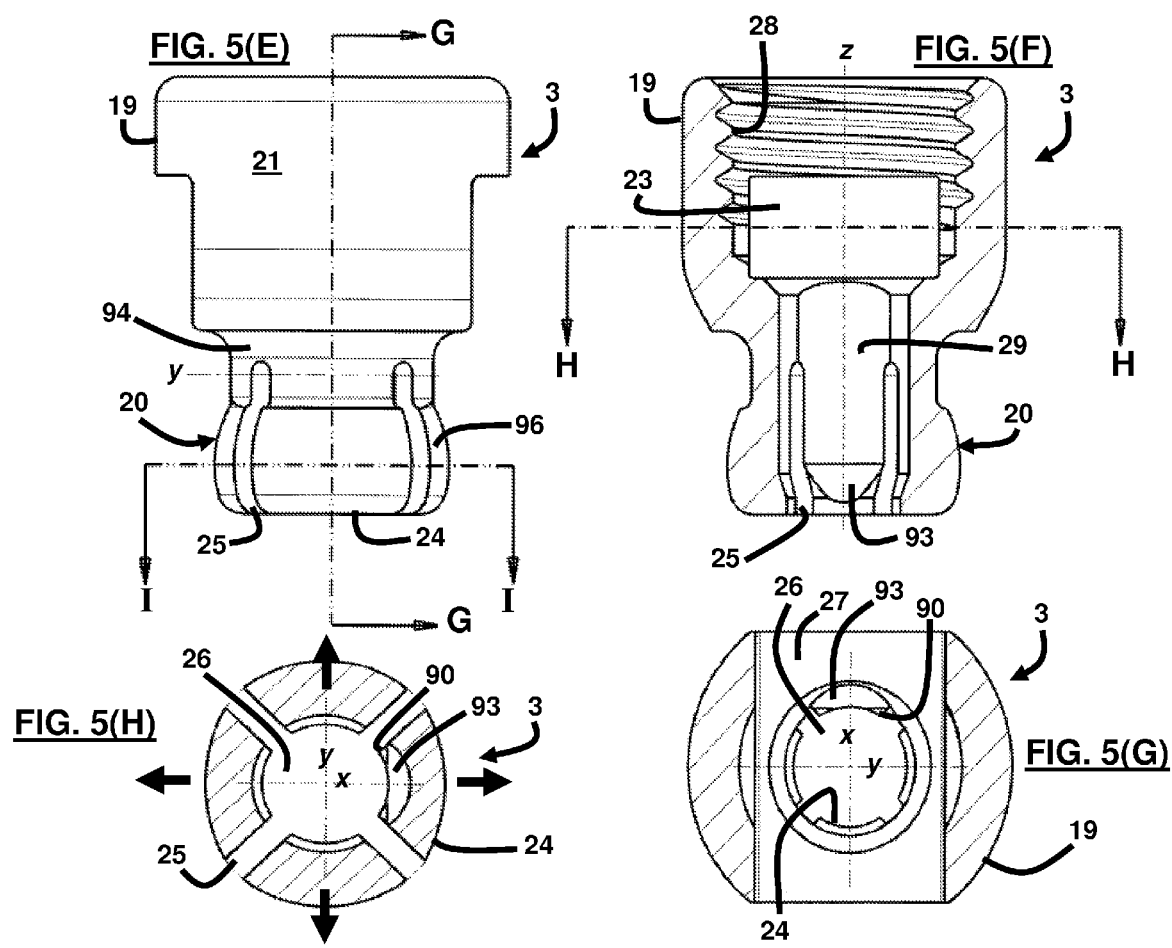

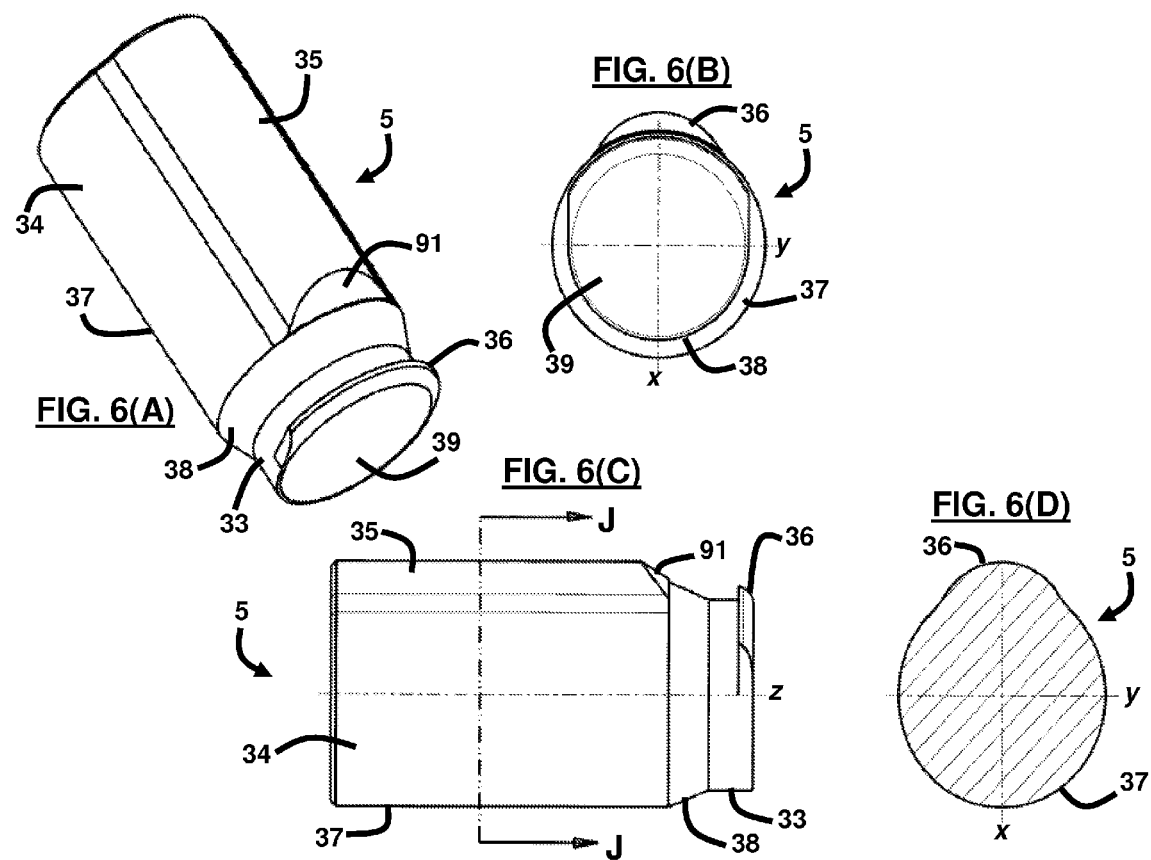

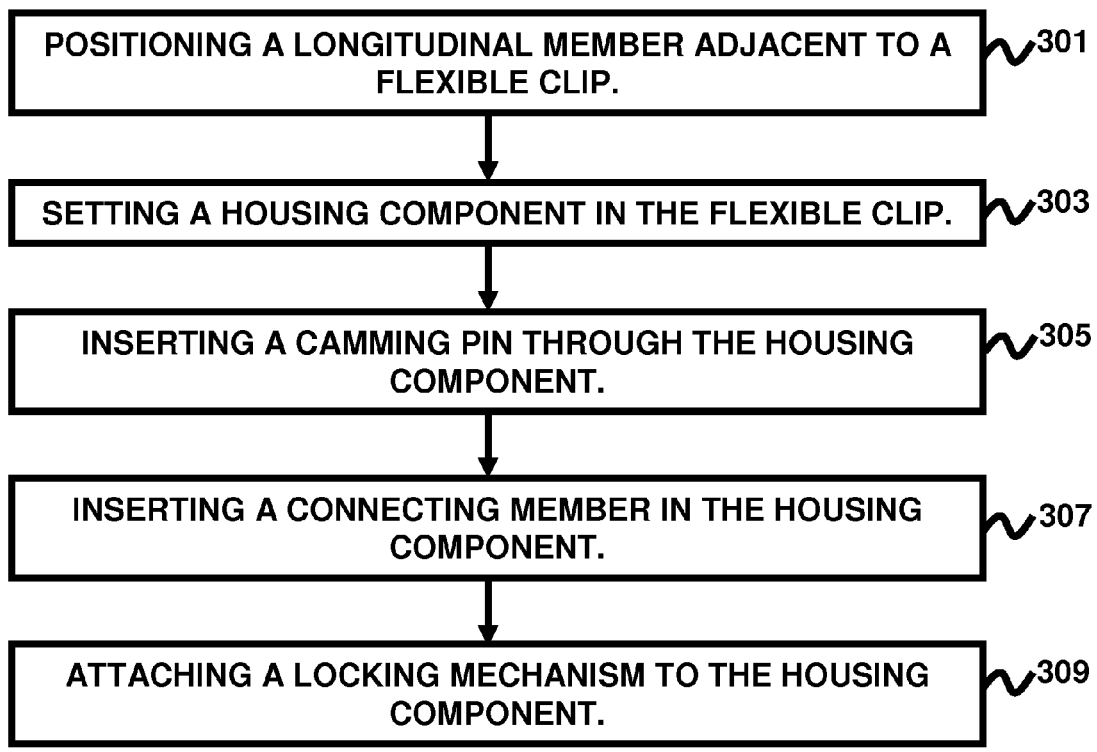

SPINAL CROSS-CONNECTOR

CROSS REFERENCE TO RELATED APPLICATION

This application is a continuation-in-part (CIP) of U.S. patent application Ser. No. 11/373,386 filed on Mar. 10, 2006 entitled "Spinal Cross-Connector" and assigned to Custom Spine, Inc. of Parsippany, N.J., the complete disclosure of which, in its entirety, is herein incorporated by reference.

BACKGROUND

1. Technical Field

The embodiments herein generally relate to medical devices, and, more particularly, to implantable spinal fixation systems used for connecting cylindrical rods to each other in spinal columns.

2. Description of the Related Art

The spinal column is a highly flexible structure comprising bones and connective tissue. While, the spine is capable of multiple degrees of motion, spinal injuries or anatomical irregularities may result in spinal pathologies which limit this range of motion. Orthopedic surgeons often aim to correct spinal irregularities and restore stability to injured portions of the spine through immobilization of spinal components. Several conventional spinal implant stabilization systems such as spinal cross-connectors exist to assist doctors in immobilizing the spine. These conventional systems often include components having connective structures such as elongated rods which are positioned on opposite sides of the portion of the spinal column intended to be immobilized and are usually implemented with screws and hooks to facilitate segmental attachment of these connective structures to the posterior surfaces of the spinal laminae, through the pedicles, and into the spinal vertebral bodies. Ideally, these connective components provide the necessary mechanical stability to achieve spinal immobilization.

Most existing spinal cross-connectors consist of rods, plates, and bars linked to the longitudinal rods by coupling mechanisms with set screws, nuts, or a combination of each. Generally, these spinal cross-connectors require several subcomponents and fixation instruments to build the structures. Each additional required component or instrument necessary to assemble the connectors typically adds to the complexity and time of the surgical procedure and may effect the successful outcome of the procedure. Examples of spinal cross-connectors are described in U.S. Pat. Nos. 5,312,405; 5,334,203; and 5,498,263, the complete disclosures of which, in their entireties, are herein incorporated by reference.

However, most conventional spinal cross-connectors generally have a limited range of motion constrained by planes or axis. This tends to make them difficult to connect to the longitudinal member (i.e., transverse rod or bar) or appropriately place them around the spinal anatomy. Spinal cross-connectors usually have 3-6 degrees of freedom of movement. Accordingly, there remains a need for a new spinal cross-connector capable of having an increased number of degrees of freedom of motion and which can be easily constructed and used by a surgeon during a spinal surgical procedure.

SUMMARY

In view of the foregoing, an embodiment herein provides an assembly comprising a longitudinal member; a flexible clip contacting the longitudinal member; a housing component contacting the flexible clip, wherein the housing component comprises a conical ramp towards a bottom end of the housing component; a locking mechanism contacting the housing component and adapted to engage the flexible clip; and a connecting member contacting the housing component. Preferably, the flexible clip comprises a flexible bias member adapted to retain the longitudinal member. Moreover, the flexible clip preferably comprises a non-symmetrical socket portion; and a clip portion attached to the non-symmetrical socket portion, the clip portion being adapted to retain the longitudinal member, wherein the flexible bias member extends from the clip portion to a bottom region of the non-symmetrical socket portion. Preferably, the locking mechanism comprises a camming pin adapted to be housed within the housing component and engage the flexible clip causing the longitudinal member to become affixed to the flexible clip; and a blocker mechanism operatively connected to the housing component and the connecting member.

Furthermore, the housing component preferably comprises an upper portion comprising a first hole adapted to engage the locking mechanism; and a second hole adapted to accommodate the connecting member, wherein the first hole and the second hole are transversely positioned with respect to one another. Moreover, the housing component preferably comprises a non-symmetrical expandable end connected to a bottom part of the upper portion, wherein the non-symmetrical expandable end comprises a plurality of flexible prongs separated from one another by slots, wherein each one of the plurality of flexible prongs comprise a bumped outer surface configured on an outer portion of each prong, and wherein one of the flexible prongs comprises the conical ramp; and an opening extending through the non-symmetrical expandable end and extending to the first hole. Additionally, the locking mechanism is preferably adapted to engage the plurality of flexible prongs causing the plurality of flexible prongs to outwardly bend and lock the housing component to the flexible clip. Also, the connecting member may comprise a slot adapted to receive the locking mechanism. Preferably, the camming pin comprises a longitudinal body portion comprising a radially extended side portion having an angled ramp; and a tip portion extending from the longitudinal body portion, wherein the tip portion comprises a unidirectional lip extending from a side of the tip portion.

Another aspect of the embodiments herein provides a spinal cross-connector assembly comprising a connector body comprising a flexible bias member; a longitudinal member locked to the connector body by the flexible bias member; a connector head adapted to engage the connector body, wherein the connector head comprises a conical ramp configured in a bottom end of the connector head; and a camming pin operatively connected to the connector body and within the connector head, wherein the camming pin comprises a longitudinal body portion comprising a protruding portion extending from a side of the longitudinal body portion, wherein the protruding portion comprises an angled ramp configured therein; and a tip portion extending from an end of the longitudinal body portion, wherein the tip portion comprises a unidirectional lip extending from a side of the tip portion, and wherein tip portion is adapted to engage the flexible bias member causing the longitudinal member to become locked to the connector body. The spinal cross-connector assembly further comprises an elongated member operatively connected to the connector head and the camming pin; and a blocker operatively connected to the connector head and the elongated member.

Preferably, the connector body comprises a non-symmetrical socket portion; and a clip portion attached to the non-symmetrical socket portion, the clip portion being adapted to retain the longitudinal member, wherein the flexible bias member extends from the clip portion to a bottom region of the non-symmetrical socket portion. Additionally, the connector head preferably comprises an upper portion comprising a first hole adapted to engage the camming pin; and a second hole adapted to accommodate the elongated member, wherein the first hole and the second hole are transversely positioned with respect to one another. Preferably, the connector head comprises a non-symmetrical expandable end connected to a bottom part of the upper portion, the non-symmetrical expandable end comprising a plurality of flexible prongs separated from one another by slots, wherein each one of the plurality of flexible prongs comprise a bumped outer surface configured on an outer portion of each prong, and wherein one of the flexible prongs comprises the conical ramp; and an opening extending through the non-symmetrical expandable end and extending to the first hole. Furthermore, the camming pin is preferably adapted to engage the plurality of flexible prongs causing the plurality of flexible prongs to outwardly bend and lock the connector head to the clip portion.

Another aspect of the embodiments herein provides a method of locking a longitudinal member to a cross-connector assembly construct, wherein the method comprises positioning a longitudinal member adjacent to a flexible clip, wherein the flexible clip comprises a flexible bias member, and wherein the flexible bias member is adapted to lock the longitudinal member to the cross-connector assembly construct; setting a housing component in the flexible clip, wherein the housing component comprises a conical ramp towards a bottom end of the housing component; and inserting a camming pin through the housing component, wherein the camming pin contacts the flexible clip, wherein the camming pin comprises a longitudinal body portion comprising a protruding portion extending from a side of the longitudinal body portion, wherein the protruding portion comprises an angled ramp configured therein; and a tip portion extending from the longitudinal body portion, wherein the tip portion comprises a unidirectional lip extending from a side of the tip portion.

The method further comprises inserting a connecting member in the housing component; and attaching a locking mechanism to the housing component, wherein the locking mechanism is operatively connected to the connecting member, wherein attachment of the locking mechanism to the housing component causes the camming pin to engage the flexible clip thereby causing the flexible clip to lock the longitudinal member into position.

Preferably, in the positioning process, the flexible clip comprises a non-symmetrical socket portion; and a clip portion attached to the non-symmetrical socket portion, the clip portion being adapted to retain the longitudinal member, wherein the flexible bias member extends from the clip portion to a bottom region of the non-symmetrical socket portion. Moreover, in the setting process, the housing component preferably comprises an upper portion and a non-symmetrical expandable end connected to a bottom part of the upper portion, wherein the upper portion comprises a first hole adapted to engage the camming pin; and a second hole adapted to accommodate the connecting member, wherein the first hole and the second hole are transversely positioned with respect to one another.

Additionally, in the setting process, the non-symmetrical expandable end preferably comprises a plurality of flexible prongs separated from one another by slots, wherein each one of the plurality of flexible prongs comprise a bumped outer surface configured on an outer portion of each prong, and wherein one of the flexible prongs comprises the conical ramp; and an opening extending through the non-symmetrical expandable end and extending to the first hole, wherein the camming pin is adapted to engage the plurality of flexible prongs causing the plurality of flexible prongs to outwardly bend and lock the non-symmetrical expandable end of the housing component to the clip portion. The method may further comprise connecting a pair of cross-connector assembly constructs using the connecting member. Also, in the inserting process, the connecting member may comprise a slot, and wherein the method further comprises inserting the camming pin through the slot of the connecting member.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 3(A) illustrates a top view of the spinal cross-connector assembly of FIG. 1 according to an embodiment herein;

FIG. 3(B) illustrates a cross-sectional view of the spinal cross-connector assembly of FIG. 3(A) cut along line A-A of FIG. 3(A) according to an embodiment herein;

FIG. 4(A) illustrates a top perspective view of the connector body of FIG. 1 according to an embodiment herein;

FIG. 4(B) illustrates a bottom perspective view of the connector body of FIG. 1 according to an embodiment herein;

FIG. 4(C) illustrates a side view of the connector body of FIG. 4(A) according to an embodiment herein;

FIG. 4(D) illustrates a cross-sectional front view of the connector body of FIG. 4(C) cut along line B-B of FIG. 4(C) according to an embodiment herein;

FIG. 4(E) illustrates a cross-sectional top view of the connector body of FIG. 4(D) cut along line C-C of FIG. 4(D) according to an embodiment herein;

FIG. 4(F) illustrates a front view of the connector body of FIG. 4(C) according to an embodiment herein;

FIG. 4(G) illustrates a cross-sectional side view of the connector body of FIG. 4(F) cut along line D-D of FIG. 4(F) according to an embodiment herein;

FIG. 4(H) illustrates a cross-sectional side view of the connector body of FIG. 4(F) cut along line E-E of FIG. 4(F) according to an embodiment herein;

FIG. 4(I) illustrates a bottom view of the connector body of FIG. 4(A) according to an embodiment herein;

FIG. 5(E) illustrates a front view of the connector head of FIG. 5(A) according to an embodiment herein;

FIG. 5(F) illustrates a cross-sectional side view of the connector head of FIG. 5(E) cut along line G-G of FIG. 5(E) according to an embodiment herein;

FIG. 5(G) illustrates a cross-sectional top view of the connector head of FIG. 5(F) cut along line H-H of FIG. 5(F) according to an embodiment herein;

FIG. 5(H) illustrates a cross-sectional top view of the connector head of FIG. 5(E) cut along line I-I of FIG. 5(E) according to an embodiment herein;

FIG. 6(A) illustrates a perspective view of the camming pin of the spinal cross-connector assembly of FIG. 2 according to an embodiment herein;

FIG. 6(B) illustrates a bottom view of the camming pin of FIG. 6(A) according to an embodiment herein;

FIG. 6(C) illustrates a front view of the camming pin of FIG. 6(A) according to an embodiment herein;

FIG. 6(D) illustrates a cross-sectional side view of the camming pin of FIG. 6(C) cut along line J-J of FIG. 6(C) according to an embodiment herein;

FIG. 9 is a flow diagram illustrating a preferred method according to an embodiment herein.

DETAILED DESCRIPTION OF PREFERRED EMBODIMENTS

Figure 1:
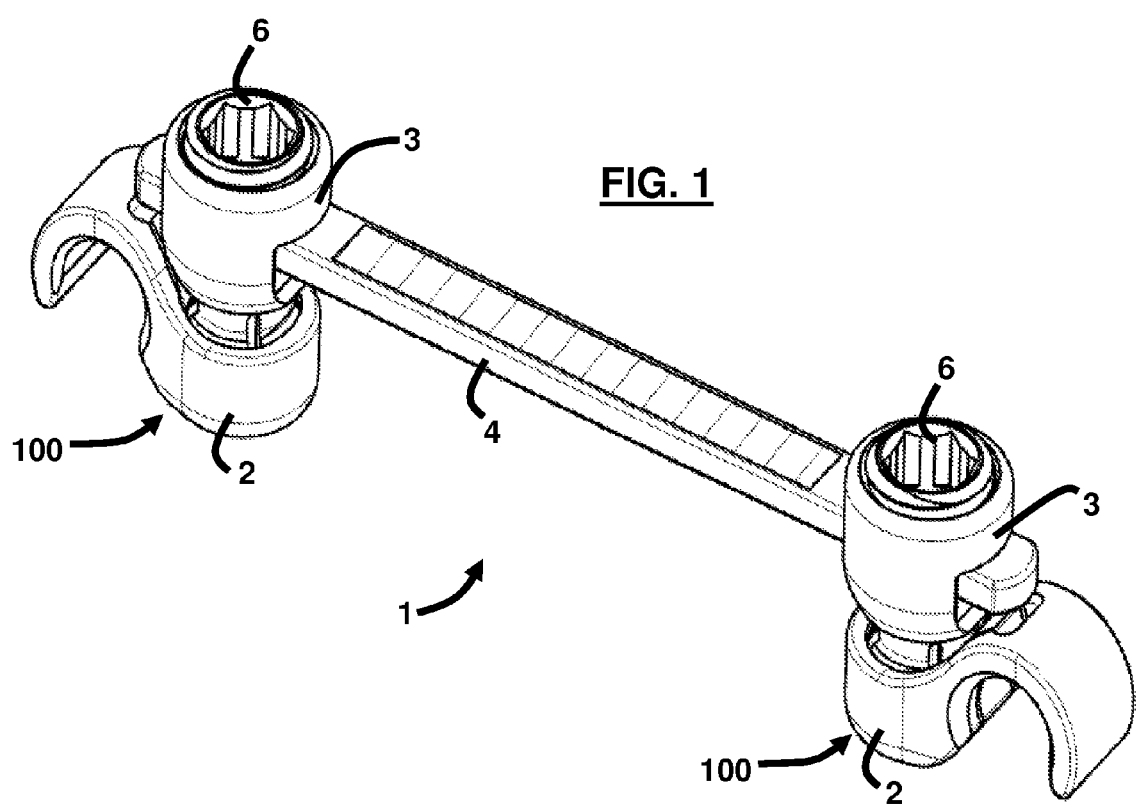
FIG. 1 illustrates a schematic diagram of a spinal cross-connector assembly system according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a new spinal cross-connector capable of having an increased number of degrees of freedom of motion and which can be easily constructed and used by a surgeon during a spinal surgical procedure. The embodiments herein achieve this by providing a top loading spinal cross-connector having a one-step locking mechanism and providing six degrees of freedom for easier placement over varied anatomy. Referring now to the drawings, and more particularly to FIGS. 1 through 9, where similar reference characters denote corresponding features consistently throughout the figures, there are shown preferred embodiments. Additionally, in several of the figures, an example orientation axis (x, y, and z axes) is given, and the descriptions below refer to these axes.

Figure 2:
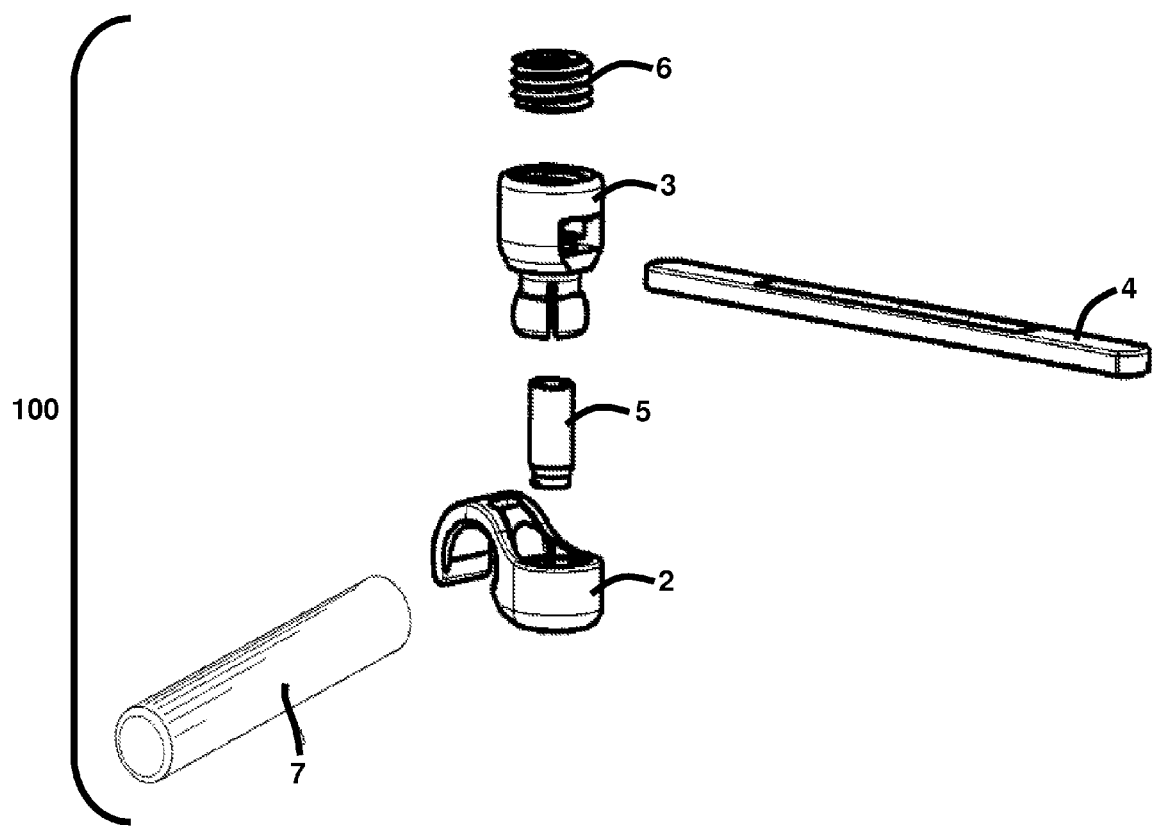
FIG. 2 illustrates an exploded view of the spinal cross-connector assembly of FIG. 1 according to an embodiment herein.

FIG. 1 illustrates a spinal cross-connector assembly 1 according to an embodiment herein. When used in a surgical procedure, the assembly 1 generally comprises two separate constructs 100 connected by a transverse member 4 (for example, a bar, rod, or other connecting elongated member geometry). As further illustrated in FIG. 2, each of the constructs 100 comprises a connector body 2 operatively connected to a connector head 3, which is dimensioned and configured to receive a camming pin 5, a set screw or blocker 6, and the transverse member 4. The connector body 2 is dimensioned and configured to engage a longitudinal member 7 (for example, a rod, bar, or other geometries). The connector body 2 is configured for use on both 6.0 and 6.35 mm diameter longitudinal members 7. With reference to FIGS. 1 and 2, both constructs 100 of the spinal cross-connector assembly 1 are placed on the opposing longitudinal members 7 of the spinal fusion construct. Preferably, each construct 100 of the spinal cross-connector assembly 1 is polyaxial with respect to its motion relative to a fixed axis and as such may be adjusted for optimum placement within the spinal cavity (not shown).

FIGS. 3(A) and 3(B) illustrate two views of one of the constructs 100 of the spinal cross-connector assembly 1 of FIG. 1. The heavy arrows in FIG. 3(B) refer to the locking forces (i.e., expansion) caused by the construct 100 when it engages the longitudinal member 7. In particular, the angled heavy arrows in FIG. 3(B) refer to the expanding forces of the connector body 2 while the heavy arrows that point down refer to the pushing force of the camming pin 5, which causes expansion of the connector head 3, which then results in the expansion of the connector body 2. These forces also aid in keeping the construct 100 in a locked position (i.e., retaining the transverse member 4 and longitudinal member 7 intact once they are set into place). All of the components (except for the longitudinal member 7) of the construct 100 can be seen in the cross-sectional view of FIG. 3(B) taken along line A-A of FIG. 3(A). In this view, the set screw 6 is set into place, which creates a downward force on the transverse member 4 and camming pin 5 to retain them into a proper set position in the connector head 3 (with the ends of the transverse member 4 extending out of the connector head 3). This view also illustrates the connector head 3 set into place within the connector body 2, which then holds the longitudinal member 7(not shown in this view) in place.

The several individual sub-components of the construct 100 of the spinal cross-connector assembly 1 of FIGS. 1 through 3(B) are further described below. FIGS. 4(A) through 4(I) illustrate several views of the connector body 2 according to an embodiment herein. The connector body 2 is generally embodied as a one-piece construct (although multiple pieces fixed to one another are possible) and comprises a socket portion 8 attached to a longitudinal member receiving clip 9. The socket portion 8 comprises a generally hollowed inner socket 10 defined by an inner socket wall 15, an inner socket base 97, and an upper lip 13. The socket portion 8 is embodied in a non-symmetrical spherical configuration. An outer socket wall 14 provides the outer definition of the socket portion 8 of the connector body 2 and further includes an outer socket base 16. The receiving clip 9 comprises a curved upper surface 11 having a concave portion 18 positioned on the underside of the curved upper surface 11. The concave portion 18 is dimensioned and configured to receive the longitudinal member 7 (of FIG. 2). In another embodiment, the receiving clip 9 is configured in a complete ring structure and is adapted to fit over the entire circumference of the longitudinal member 7 (of FIG. 2).

The inner socket base 97 of the socket portion 8 is generally bowl-shaped and it is on this base 97 where the connector head 3 and camming pin 5 (of FIGS. 1 and 2) rest. The inner socket base 97 further includes a gap 17, which creates a separation between the inner socket base 97 and a bias member 12 of the connector body 2. The bias member 12 may be configured as a spring, flange, or flexible structure. The gap 17 extends up to a notch 99 in the curved upper surface 11 in the receiving clip 9. The notch 99 is dimensioned and configured to receive an end 31, 32 of the transverse member 4 (shown in FIG. 1 and 8(A) through 8(C)). Generally, the bias member 12 is an extension of the receiving clip 9 as it is retained in a cantilever manner to the connector body 2 only by the receiving clip 9 and does not contact the socket portion 8 due to the gap 17. Preferably, the thickness of the gap 17 is uniform, but may include a slightly larger gap area towards the bottom of the gap 17.

FIG. 4(D) illustrates a cross-sectional front view of the connector body 2 of FIG. 4(C) taken along line B-B of FIG. 4(C). FIG. 4(F) illustrates a front view of the connector body 2 of FIG. 4(C). In these views, the relative thicknesses of the socket portion 8 and receiving clip 9 can be seen as well as the relative depth of the gap 17. Additionally, the configuration of the concave portion 18 of the receiving clip 9 can be seen as generally matching the cylindrical configuration of the longitudinal member 7 (of FIG. 2). FIG. 4(E) illustrates a cross-sectional top view of the connector body 2 of FIG. 4(A) taken along line C-C of FIG. 4(D) and FIG. 4(I) illustrates a bottom view of the connector body 2 of FIG. 4(A), and these views further illustrate the general configuration of the gap 17 and the generally spherical arcs 98 leading towards the inner socket base 97. For example, there are four spherical arcs 98 that are configured to create the non-uniform inner socket 10 to constrain the motion of the connector head 3 (of FIGS. 5(A) through 5(H)). The connector head 3 can still rotate slightly around the z-axis, but the non-symmetrical inner socket 10 keeps the connector head 3 aligned for locking purposes. This is so that when the camming pin 5 (of FIGS. 6(A) through 6(D)) is driven through the connector head 3 to indirectly expand the bias member 12 such that no locking forces are lost in the process.

FIG. 4(G) illustrates a cross-sectional side view of the connector body 2 of FIG. 4(F) cut along line D-D of FIG. 4(F) and FIG. 4(H) illustrates a cross-sectional side view of the connector body 2 of FIG. 4(F) cut along line E-E of FIG. 4(F). These views illustrate the general contour of the connector body 2. When viewed from the side as in FIG. 4(H), the gap 17 may appear as a bell shape. However, the gap 17 may be configured in any appropriate shape, and the embodiments herein are not limited to any particular shape or geometry.

FIGS. 5(A) through 5(H) illustrate several views of the connector head 3 of the spinal cross-connector assembly construct 100 of FIG. 2 according to an embodiment herein. Preferably, the connector head 3 is a one-piece construct (although multiple pieces fixed to one another are possible) and comprises an upper portion 19 that is connected to neck portion 94 that is connected to a lower non-symmetrical expandable end 20 outwardly projecting from the neck portion 94. The upper portion 19 is defined by a generally curved outer wall 21 having an upper cavity hole 22 and a bar receiving hole 23 configured therein. Preferably, the upper cavity hole 22 is positioned along a longitudinal axis of the connector head 3 and the bar receiving hole 23 is positioned along an axis transverse to the longitudinal axis of the connector head 3, and thus the upper cavity hole 22 is preferably transverse to the bar receiving hole 23. The bar receiving hole 23 extends through the outer wall 21 of the connector head 3 and the upper cavity hole 22 extends longitudinally through the connector head 3 and terminates with an opening 26 at the bottom of the expandable end 20 of the connector head 3. Threads 28 are configured in the upper portion 19 of the connector head 3 and are dimensioned and configured to receive the set screw 6 (of FIGS. 2 and 7(A) through 7(D)). Preferably the threads 28 are configured inside the upper portion 19 of the connector head 3, but in another embodiment may be configured on the outer wall 21 of the upper portion 19 of the connector head to accommodate different configurations of the set screw 6 (of FIGS. 2 and 7(A) through 7(D)).

An inner connector base 27 generally separates the upper portion 19 of the connector head 3 from neck portion 94 of the connector head 3, wherein the inner connector base 27 is preferably flat to facilitate an even positioning of the transverse member 4 (of FIGS. 2 and 8(A) through 8(C)). Moreover, the expandable end 20 preferably comprises a generally cylindrical configuration having a plurality of outwardly-turned prongs 24 spaced apart from one another by slots 25. The prongs 24 are flexible to allow expansion of the expandable end 20 of the connector head 3 into the inner socket 10 of the connector body 2 (of FIGS. 2 and 4(A) through 4(I)). The prongs 24 have an outwardly projecting surface 96 having a lip 95 that serves a catch to lock the connector head 3 within the inner socket 10 of the connector body 2 (of FIGS. 2 and 4(A) through 4(I)). One of the prongs 24 is configured differently from the other prongs. This different prong (called the cam flange 90) comprises a conical ramp 93 configured thereon. The conical ramp 93 comprises an angled cut that provides a ramp for the angled ramp 91 (of FIGS. 6(A) and 6(C)). FIGS. 5(F) through 5(H) further illustrate the conical ramp 93 configured towards only one side of the bottom of the pin cavity 29 such that the conical ramp 93 rests on the cam flange 90.

Additionally, a pin cavity 29 is configured in the expandable end 20 of the connector head 3 to accommodate the camming pin 5 (of FIGS. 2 and 6(A) through 6(D)), wherein the upper part of the pin cavity 29 begins at the position of the inner connector base 27, and the lower part of the pin cavity 29 terminates at the opening 26 in the expandable end 20 of the connector head 3. The pin cavity 29 may be embodied in any appropriate configuration so long as it can accommodate a corresponding configuration of the camming pin 5 (of FIGS. 6(A) through 6(D)).

Figure 5A:
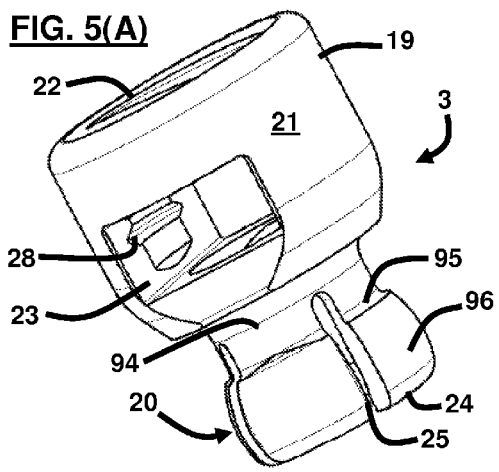
FIG. 5(A) illustrates a perspective view of the connector head of the spinal cross-connector assembly of FIG. 1 according to an embodiment herein.
Figure 5B:
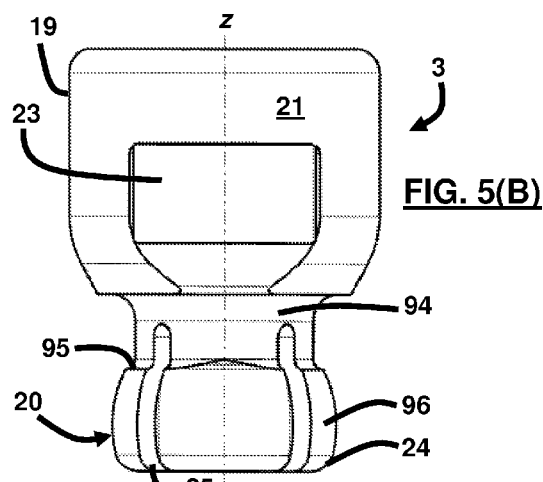
FIG. 5(B) illustrates a side view of the connector head of FIG. 5(A) according to an embodiment herein.
Figure 5C:
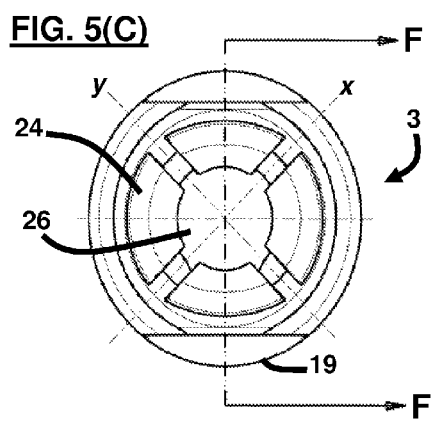
FIG. 5(C) illustrates a bottom view of the connector head of FIG. 5(A) according to an embodiment herein.
Figure 5D:
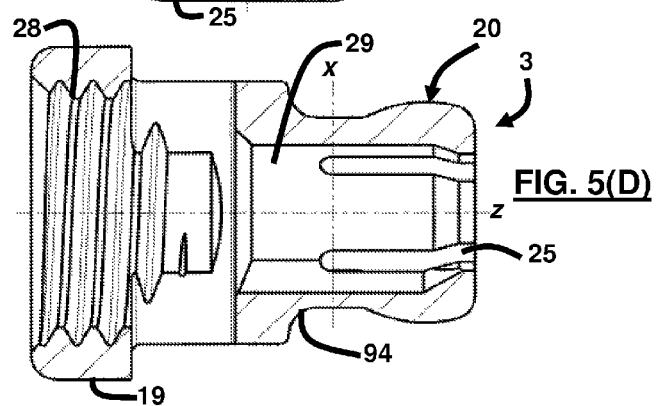
FIG. 5(D) illustrates a cross-sectional front view of the connector head of FIG. 5(C) cut along line F-F of FIG. 5(C) according to an embodiment herein.

FIG. 5(D) illustrates a cross-sectional front view of the connector head 3 of FIG. 5(C) cut along line F-F of FIG. 5(C). Moreover, FIG. 5(F) illustrates a cross-sectional side view of the connector head 3 of FIG. 5(E) cut along line G-G of FIG. 5(E). Furthermore, FIG. 5(G) illustrates a cross-sectional top view of the connector head 3 of FIG. 5(F) cut along line H-H of FIG. 5(F). Additionally, FIG. 5(H) illustrates a cross-sectional top view of the connector head 3 of FIG. 5(E) cut along line I-I of FIG. 5(E). In these views, the relative thickness of the upper portion 19 of the connector head 3 is illustrated as well as the configurations of the threads 28 and pin cavity 29.

The inner portion (towards the opening 26) of the expandable end 20 is also non-symmetrical due to the conical ramp 93, and matches the geometric configuration of the inner socket 10 of the connector body 2 (of FIGS. 4(A) through 4(I)). Together, the expandable end 20 of the connector head 3 and the inner socket 10 of the connector body 2 constrain the rotation around the z-axis to ensure that the cam flange 96 is always oriented with the bias member 12 of the connector body 2 to ensure proper functioning of the assembly 1 (of FIG. 1).

FIGS. 6(A) through 6(D) illustrate several views of the camming pin 5 of the spinal cross-connector assembly construct 100 of FIG. 2 according to an embodiment herein. The camming pin 5 is preferably embodied as a one-piece construct (although multiple pieces fixed to one another are possible). The camming pin 5 comprises an upper end 37 that is connected to a sloping middle portion 38 that is connected to lower end 33 terminating with a substantially flat end 39. The upper end 37 has an interrupted cylindrically longitudinal shape having a curved outer wall 34. One side of the curved outer wall 34 comprises a protruding portion 35 extending therefrom, wherein the protruding portion 35 comprises an angled ramp 91 configured therein. The angled ramp 91 is configured to create a ramp for smooth interaction with the conical ramp 93 of the cam flange 90. The configuration of the upper end 37 provides increased locking in one direction (direction where the protruding portion 35 is). Additionally, the lower end 33 comprises a unidirectional lip 36 extending from a side of the lower end 33. The lip 36 allows for permanent assembly of the camming pin 5 in the inner socket 10 of the connector head 3. The lower end 33 and lip 36 are adapted to engage the flexible bias member 12 of the connector body 2 (of FIGS. 4(A) through 4(I)) causing the longitudinal member 7 (of FIG. 2) to become locked by the receiving clip 9 of the connector body 2 (of FIGS. 4(A) through 4(I)).

Preferably, the overall contour of the camming pin 5 is dimensioned and configured to fit into the pin cavity 29 of the connector head 3 (of FIGS. 5(A) through 5(H)). FIG. 6(D) illustrates a cross-sectional side view of the camming pin 5 of FIG. 6(C) cut along line J-J of FIG. 6(C). In this view, the contour of the lip 36 with respect to the upper end 37 can be seen (although other contours and shapes are possible so long as they match the corresponding configuration of the pin cavity 29 of the connector head 3 (of FIGS. 5(A) through 5(H)).

Figure 7A:
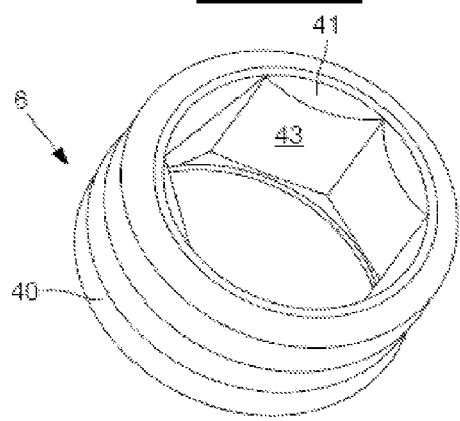
FIG. 7(A) illustrates a perspective view of the blocker of the spinal cross-connector assembly of FIG. 1 according to an embodiment herein.
Figure 7B:
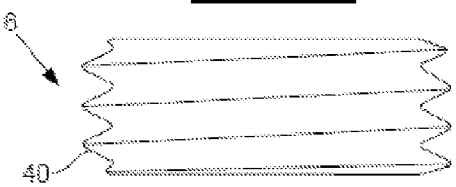
FIG. 7(B) illustrates a side view of the blocker of FIG. 7(A) according to an embodiment herein.
Figure 7C:
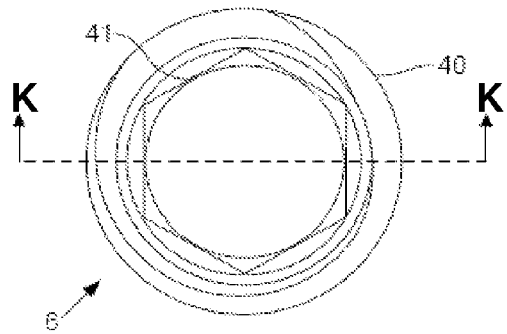
FIG. 7(C) illustrates a top view of the blocker of FIG. 7(A) according to an embodiment herein.
Figure 7D:
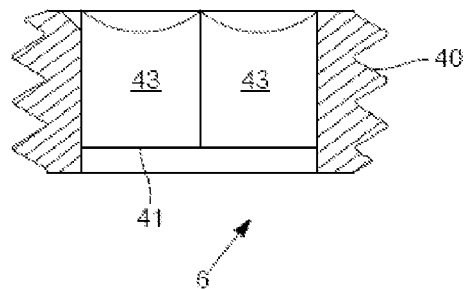
FIG. 7(D) illustrates a cross-sectional side view of the blocker of FIG. 7(C) cut along line K-K of FIG. 7(C) according to an embodiment herein.

FIGS. 7(A) through 7(D) illustrate several views of the set screw 6 of the spinal cross-connector assembly 1 of FIG. 1 according to an embodiment herein. Generally, the set screw 6 may be any type of blocker used to retain the transverse member 4 and camming pin 5 in place in the connector head 3 (of FIGS. 2 and 5(A) through 5(H)). In one embodiment, the set screw 6 comprises threads 40 positioned around an outer periphery of the set screw 6 and dimensioned and configured to engage the threads 28 of the connector head 3 (of FIGS. 5(A) through 5(H)). Moreover, the set screw 6 comprises a fastening feature 41, which may be configured to accommodate a screwdriver (hex, torx, flat-head, Phillips, etc.) or similar mechanism. Alternatively, as previously mentioned if the threads 28 of the connector head 3 (of FIGS. 5(A) through 5(H)) are configured along the outer wall 21 of the connector head 3, then the corresponding threads 40 of the set screw 6 are configured along the inner wall 43 of the set screw 6 of FIG. 7(A). FIG. 7(D) illustrates a cross-sectional side view of the set screw 6 of FIG. 7(A) cut along line K-K of FIG. 7(C), which further shows the inner wall 43 of the set screw 6.

Figure 8A:
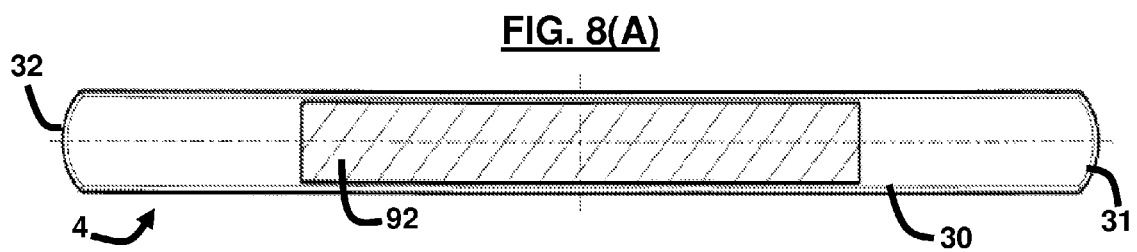
FIG. 8(A) illustrates a top view of the cross-connecting bar of the spinal cross-connector assembly of FIG. 1 according to an embodiment herein.
Figure 8B:
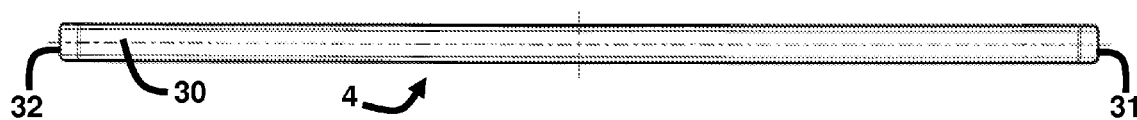
FIG. 8(B) illustrates a front view of the cross-connecting bar of FIG. 8(A) according to an embodiment herein.
Figure 8C:
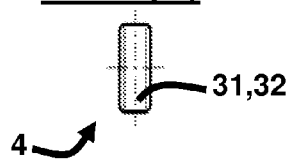
FIG. 8(C) illustrates a side view of the cross-connecting bar of FIG. 8(A) according to an embodiment herein.

FIGS. 8(A) through 8(C) illustrate several views of the transverse member 4 (of FIGS. 1 and 2) according to an embodiment herein. The transverse member 4 generally comprises a generally uniform elongated one-piece body 30 (although multiple pieces fixed to one another are possible) with a pair of distal ends 31, 32 comprising a first end 31 distally located to a second end 32. The transverse member 4 is dimensioned and configured to fit through the bar receiving hole 23 of the connector head 3 and rest on the inner socket base 16 of the connector head 3 (of FIGS. 5(A) through 5(H)). The bar receiving hole 23 may be configured to snugly fit the transverse member 4, or alternatively, the bar receiving hole 23 may be configured wider than the width of the transverse member 4 to allow for some "slop" for additional range of motion of the transverse member 4. A serrated portion 92 may also be configured on the body 30 of the transverse member 4. In other alternate embodiments, the transverse member 4 may comprise a slot (not shown) configured in the body 30.

With respect to FIGS. 1 through 8(C), in a preferred embodiment, the transverse member 4 is bendable and may be bent if desired to avoid interference with the spinal anatomy (not shown). Moreover, the bendable transverse member 4 may be cut to length if desired to avoid protrusion into soft tissue or can be pre-cut and pre-assembled to various sizes. Furthermore, each polyaxial connector head 3 is locked into place by its internal preloaded set screw 6.

Accordingly, the set screw 6 locks the polyaxial connector head 3 into position as well as the connector body 2 to the longitudinal member 7 all in one locking step. This occurs by placing the expandable end 20 of the connector head 3 into the inner socket 10 of the socket portion 8 of the connector body 2. Next, the camming pin 5 is placed into the pin cavity 29 (lower end 33 of the camming pin 5 is placed first) of the connector head 3. Then, the transverse member 4 is placed in the bar receiving hole 23 of the connector head 3. Thereafter, the longitudinal member 7 is placed into position in the concave portion 18 of the receiving clip 9 of the connector body 2.

After this, in a one-step locking procedure, the set screw 6 is fastened into place in the connector head 3 with the threads 40 of the set screw 6 engaging the threads 28 of the connector head 3. The tightening of the set screw 6 causes the body 30 of the transverse bar 4 to exert a force on the camming pin 5, which causes the lip 36 of the lower end 33 of the camming pin 5 to exert a force on the prongs 24 of the expandable end 20 of the connector head 3, which causes the expandable end 20 of the connector head 3 to expand in the inner socket 10 of the socket portion 8 of the connector body 2. This also causes the lip 36 to protrude through the opening 26 of the expandable end 20 of the connector head 3. This, in turn, causes the bias member 12 of the connector body 2 to bend away from the connector head 3 and against the longitudinal member 7, which is positioned in the concave portion 18 of the receiving clip 9 of the connector body 2 thereby securing the longitudinal member 7 into a set position in the concave portion 18 of the receiving clip 9. As such, this locking procedure locks the connector head 3 and longitudinal member 7 to the connector body 2 as well as the transverse member 4 and camming pin 5 to the connector head 3.

The conical ramp 93 of the cam flange 90 and the camming pin 5 interact with one another to provide non-symmetric locking forces and no uniform expansion of the prongs 24. The non-uniform expansion of the cam flange 90 causes increased direct expansion of the bias member 12 providing the locking feature of the connector body 2 to the longitudinal member 7 of the construct 100.

In other alternative embodiments, the geometry of the connector body 2 may be modified for customized angle placement of the longitudinal member 7 on the connector body 2. Additionally, the inner socket 10 of the connector body 2 may be positioned at various locations in the connector body 2 to provide varied offsets or heights of initial position for the assembly 1. Also, the elongated connecting transverse member 4 may be dimensioned and configured to fit over the connector head 3 and be locked by the set screw 6. Furthermore, the materials for all components in the assembly 1 may comprise any suitable grades of metal, polymers, or shape-memory materials.

FIG. 9, with reference to FIGS. 1 through 8(C), illustrates a flow diagram of a method of locking a longitudinal member 7 to a cross-connector assembly construct 100, wherein the method comprises positioning (301) a longitudinal member 7 adjacent to a flexible clip 2, wherein the flexible clip 2 comprises a flexible bias member 12, and wherein the flexible bias member 12 is adapted to lock the longitudinal member 7 to the cross-connector assembly construct 100; setting (303) a housing component 3 in the flexible clip 2, wherein the housing component 3 comprises a conical ramp 93 towards a bottom end of the housing component 3; and inserting (305) a camming pin 5 through the housing component 3, wherein the camming pin 5 contacts the flexible clip 2, wherein the camming pin 5 comprises a longitudinal body portion 37 comprising a protruding portion 35 extending from a side of the longitudinal body portion 37, wherein the protruding portion 35 comprises an angled ramp 91 configured therein; and a tip portion 33 extending from the longitudinal body portion 37, wherein the tip portion 33 comprises a unidirectional lip 36 extending from a side of the tip portion 33.

The method further comprises inserting (307) a connecting member 4 in the housing component 3; and attaching (309) a locking mechanism 6 to the housing component 3, wherein the locking mechanism 6 is operatively connected to the connecting member 4, wherein attachment of the locking mechanism 6 to the housing component 3 causes the camming pin 5 to engage the flexible clip 2 thereby causing the flexible clip 2 to lock the longitudinal member 7 into position.

Preferably, in the positioning process (301), the flexible clip 2 comprises a non-symmetrical socket portion 8; and a clip portion attached to the non-symmetrical socket portion 8, the clip portion being adapted to retain the longitudinal member 7, wherein the flexible bias member 12 extends from the clip portion to a bottom region of the non-symmetrical socket portion 8. Moreover, in the setting process (303), the housing component 3 preferably comprises an upper portion 19 and a non-symmetrical expandable end 20 connected to a bottom part 94 of the upper portion 19, wherein the upper portion 19 comprises a first hole 29 adapted to engage the camming pin 5; and a second hole 23 adapted to accommodate the connecting member 4, wherein the first hole 29 and the second hole 23 are transversely positioned with respect to one another.

Additionally, in the setting process (303), the non-symmetrical expandable end 20 preferably comprises a plurality of flexible prongs 24 separated from one another by slots 25, wherein each one of the plurality of flexible prongs 25 comprise a bumped outer surface 96 configured on an outer portion of each prong 24, and wherein one of the flexible prongs 90 comprises the conical ramp 93; and an opening 26 extending through the non-symmetrical expandable end 20 and extending to the first hole 29, wherein the camming pin 5 is adapted to engage the plurality of flexible prongs 24 causing the plurality of flexible prongs 24 to outwardly bend and lock the non-symmetrical expandable end 20 of the housing component 3 to the clip portion. The method may further comprise connecting a pair of cross-connector assembly constructs 100 using the connecting member 4. Also, in the inserting process (307), the connecting member 4 may comprise a slot (not shown), and wherein the method further comprises inserting the camming pin 5 through the slot (not shown) of the connecting member 4.

The assembly 1 of FIG. 1 is assembled with proper orientation of the subcomponents. This is because of the non-uniform expansion and non-symmetric locking of the subcomponents. Preferably, the deflection and subsequent locking forces in the y-plane are equal. Moreover, the deflection and locking forces in the x-plane are not equal due to the configuration that is implemented for both the connector head 3 and the camming pin 5.

Generally, the embodiments herein provide a polyaxial cross-connector (transverse connector/rod crosslink) assembly 1 adapted to connect the longitudinal members 7 of a spinal fusion construct 100 in an easy an efficient manner. The embodiments herein augment the conventional assemblies by providing an assembly that is stiffer and stronger under torsional loads than conventional designs. The assembly 1 generally comprises a flexible clip 9 with a socket 10 adapted to receive the polyaxial connector head 2 which houses the bendable transverse member 4. Moreover, the embodiments herein have a minimum of two to a maximum of nine degrees (and preferably six degrees) of freedom depending on whether the bendable transverse member 4 is embodied as a rod or bar. Furthermore, the assembly 1 may be packaged pre-assembled prior to use during surgery.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. An assembly comprising:
a longitudinal member;
a flexible clip contacting said longitudinal member;
a connecting member;
a housing component contacting said flexible clip and said connecting member, wherein said housing component comprises:
an upper portion comprising:
a first continuous cylindrical hole bored through said housing component and engaging said locking mechanism, wherein the first hole is bored along a longitudinal axis of said housing component; and
a second continuous uniform hole bored through said upper portion and accommodating said connecting member, wherein the second hole is bored along a lateral axis of said housing component,
wherein said longitudinal axis of said first hole and said lateral axis of said second hole intersect one another;
a conical ramp embedded in said first hole and positioned between a bottom end of said housing component and the intersection of said longitudinal axis of said first hole and said lateral axis of said second hole; and
a locking mechanism contacting said housing component, wherein said locking mechanism engages said flexible clip.

2. The assembly of claim 1, wherein said flexible clip comprises a flexible bias member adapted to retain said longitudinal member.

3. The assembly of claim 2, wherein said flexible clip comprises:
a non-symmetrical socket portion; and
a clip portion attached to said non-symmetrical socket portion, wherein said clip portion retains said longitudinal member,
wherein said flexible bias member extends from said clip portion to a bottom region of said non-symmetrical socket portion.

4. The assembly of claim 2, wherein said locking mechanism comprises:
a camming pin housed within said housing component and engaging said flexible clip causing said longitudinal member to become affixed to said flexible clip; and
a blocker mechanism operatively connected to said housing component and said connecting member.

5. The assembly of claim 1, wherein said housing component further comprises threads etched into said housing component between a top end and the intersection of said longitudinal axis of said first hole and said lateral axis of said second hole.

6. The assembly of claim 1, wherein said housing component comprises an expandable end connected to a bottom part of said upper portion, said expandable end comprising:
a plurality of flexible prongs separated from one another by slots, wherein each one of said plurality of flexible prongs comprise a bumped outer surface configured on an outer portion of each prong, and wherein one of the flexible prongs comprises said conical ramp; and
an opening extending through said expandable end and extending to said first hole.

7. The assembly of claim 6, wherein said locking mechanism engages said plurality of flexible prongs causing said plurality of flexible prongs to outwardly bend and lock said housing component to said flexible clip.

8. The assembly of claim 1, wherein said connecting member comprises a slot that receives said locking mechanism.

9. The assembly of claim 4, wherein said camming pin comprises:
a longitudinal body portion comprising a radially extended side portion having an angled ramp; and
a tip portion extending from said longitudinal body portion, wherein said tip portion comprises a unidirectional lip extending from a side of said tip portion.

10. A spinal cross-connector assembly comprising:
a connector body comprising a flexible bias member;
a longitudinal member locked to said connector body by said flexible bias member;
an elongated member operatively connected to said connector head and said camming pin;
a camming pin operatively connected to said connector body and within said connector head, wherein said camming pin comprises:
a longitudinal body portion comprising a protruding portion extending from a side of said longitudinal body portion, wherein said protruding portion comprises an angled ramp configured therein; and
a tip portion extending from an end of said longitudinal body portion, wherein said tip portion comprises a unidirectional lip extending from a side of said tip portion, and wherein tip portion engages said flexible bias member causing said longitudinal member to become locked to said connector body;
a connector head that engages said connector body, wherein said connector head comprises:
an upper portion comprising:
a first continuous cylindrical hole bored through said housing component and engaging said locking mechanism, wherein the first hole is bored along a longitudinal axis of said housing component; and
a second continuous hole bored through said upper portion and accommodating said connecting member, wherein the second hole is bored along a lateral axis of said housing component, wherein said second hole is defined by a length and a width such that the length of said second hole is limited to a lateral length of said housing component,
wherein said longitudinal axis of said first hole and said lateral axis of said second hole intersect one another perpendicularly; and
a conical ramp configured in said first hole and between a bottom end of said connector head and the intersection of said longitudinal axis of said first hole and said lateral axis of said second hole; and
a blocker operatively connected to said connector head and said elongated member.

11. The spinal cross-connector assembly of claim 10, wherein said connector body comprises:
a non-symmetrical socket portion; and
a clip portion attached to said non-symmetrical socket portion, wherein said clip portion retains said longitudinal member, wherein said flexible bias member extends from said clip portion to a bottom region of said non-symmetrical socket portion.

12. The spinal cross-connector assembly of claim 10, wherein said connector head comprises threads etched into said connector head between a top end and said intersection of said longitudinal axis of said first hole and said lateral axis of said second hole.

13. The spinal cross-connector assembly of claim 10, wherein said connector head comprises an expandable end connected to a bottom part of said upper portion, said expandable end comprising:
a plurality of flexible prongs separated from one another by slots, wherein each one of said plurality of flexible prongs comprise a bumped outer surface configured on an outer portion of each prong, and wherein one of the flexible prongs comprises said conical ramp; and
an opening extending through said expandable end and extending to said first hole.

14. The spinal cross-connector assembly of claim 13, wherein said camming pin engages said plurality of flexible prongs causing said plurality of flexible prongs to outwardly bend and lock said connector head to said clip portion.

15. A method of locking a longitudinal member to a cross-connector assembly construct, said method comprising:
positioning a longitudinal member adjacent to a flexible clip, wherein said flexible clip comprises a flexible bias member, and wherein said flexible bias member locks said longitudinal member to said cross-connector assembly construct;
setting a housing component in said flexible clip, wherein said housing component comprises:
an upper portion comprising:
a first continuous cylindrical hole bored through said housing component and engaging said locking mechanism, wherein the first hole is bored along a longitudinal axis of said housing component; and
second continuous hole bored through said upper portion and accommodating a connecting member, wherein the second hole is bored along a lateral axis of said housing component, wherein said second hole is defined by a length and a width such that a thickness of said width is uniform along an entire lateral length of said second hole, wherein said longitudinal axis of said first hole and said lateral axis of said second hole intersect one another perpendicularly; and a conical ramp embedded in said first hole, between a bottom end of said housing component and the intersection of said longitudinal axis of said first hole and said lateral axis of said second hole;

inserting a camming pin through said housing component, wherein said camming pin contacts said flexible clip, wherein said camming pin comprises:

a longitudinal body portion comprising a protruding portion extending from a side of said longitudinal body portion, wherein said protruding portion comprises an angled ramp configured therein; and a tip portion extending from said longitudinal body portion, wherein said tip portion comprises a unidirectional lip extending from a side of said tip portion;

inserting said connecting member in said housing component; and attaching a locking mechanism to said housing component, wherein said locking mechanism is operatively connected to said connecting member, wherein attachment of said locking mechanism to said housing component causes said camming pin to engage said flexible clip thereby causing said flexible clip to lock said longitudinal member into position.

16. The method of claim 15, wherein in the positioning process, said flexible clip comprises:

a non-symmetrical socket portion; and a clip portion attached to said non-symmetrical socket portion, wherein said clip portion retains said longitudinal member, wherein said flexible bias member extends from said clip portion to a bottom region of said non-symmetrical socket portion.

17. The method of claim 16, wherein in the setting process, said housing component further an expandable end connected to a bottom part of said upper portion.

18. The method of claim 17, wherein in the setting process, said expandable end comprises:

a plurality of flexible prongs separated from one another by slots, wherein each one of said plurality of flexible prongs comprise a bumped outer surface configured on an outer portion of each prong, and wherein one of the flexible prongs comprises said conical ramp; and an opening extending through said expandable end and extending to said first hole, wherein said camming pin engages said plurality of flexible prongs causing said plurality of flexible prongs to outwardly bend and lock said expandable end of said housing component to said clip portion.

19. The method of claim 15, further comprising connecting a pair of cross-connector assembly constructs using said connecting member.

20. The method of claim 15, wherein in the inserting process, said connecting member comprises a slot, and wherein said method further comprises inserting said camming pin through said slot of said connecting member.

* * * * *